(12) United States Patent
Sutoh et al.

(10) Patent No.: US 8,679,002 B2
(45) Date of Patent: Mar. 25, 2014

(54) ENDOSCOPE SYSTEM FOR GASTROSTOMY CATHETER PLACEMENT

(75) Inventors: Dai Sutoh, Fukuroi (JP); Kazuhiro Abe, Fukuroi (JP)

(73) Assignee: Covidien LP, Mansfield, MA (US)

( * ) Notice: Subject to any disclaimer, the term of this patent is extended or adjusted under 35 U.S.C. 154(b) by 1100 days.

(21) Appl. No.: 12/277,090

(22) Filed: Nov. 24, 2008

(65) Prior Publication Data

US 2009/0143648 A1 Jun. 4, 2009

(30) Foreign Application Priority Data

Nov. 30, 2007 (JP) ................................ 2007-310654

(51) Int. Cl.
*A61B 1/00* (2006.01)
*A61B 1/04* (2006.01)

(52) U.S. Cl.
USPC ............................ 600/121; 600/114; 600/139

(58) Field of Classification Search
USPC .................................. 600/114–116, 121, 125
See application file for complete search history.

(56) References Cited

U.S. PATENT DOCUMENTS

| | | | | |
|---|---|---|---|---|
| 4,646,722 | A | | 3/1987 | Silverstein et al. |
| 4,685,901 | A | | 8/1987 | Parks |
| 4,869,238 | A | | 9/1989 | Opie et al. |
| 4,991,565 | A | | 2/1991 | Takahashi et al. |
| 5,050,585 | A | | 9/1991 | Takahashi |
| 5,301,061 | A | * | 4/1994 | Nakada et al. ................ 359/362 |
| 5,337,734 | A | * | 8/1994 | Saab ............................ 600/121 |
| 5,413,092 | A | * | 5/1995 | Williams et al. .............. 600/125 |
| 5,643,175 | A | | 7/1997 | Adair |
| 5,916,147 | A | * | 6/1999 | Boury .......................... 600/146 |
| 5,924,977 | A | | 7/1999 | Yabe et al. |
| 6,007,482 | A | | 12/1999 | Madni et al. |
| 6,013,024 | A | * | 1/2000 | Mitsuda et al. ............... 600/146 |
| 6,224,565 | B1 | | 5/2001 | Cimino |
| 6,749,584 | B2 | | 6/2004 | Briggs et al. |
| 6,793,661 | B2 | | 9/2004 | Hamilton et al. |
| 6,929,601 | B2 | | 8/2005 | Nakao |
| 6,991,602 | B2 | * | 1/2006 | Nakazawa et al. ............ 600/101 |
| 7,060,050 | B2 | | 6/2006 | Kliem et al. |

(Continued)

FOREIGN PATENT DOCUMENTS

| | | |
|---|---|---|
| JP | 03-059509 | 3/1991 |
| JP | 03292925 A | 12/1991 |

(Continued)

OTHER PUBLICATIONS

European Search Report regarding related application serial No. EP 08170169.0 dated Mar. 6, 2009, 6 pgs.

(Continued)

*Primary Examiner* — Alireza Nia

(57) ABSTRACT

An instrument for confirming the position of an indwelling gastrostomy catheter, and a method of confirming the indwelling position thereof, with which it is possible to reduce cleaning costs, and which does not cause any discomfort to a patient. An instrument for confirming the indwelling position of a gastrostomy catheter which is indwelling in a hole formed between the surface of the skin of the patient and the inner surface of the stomach wall comprising a fiberscope and a protective cover. Furthermore, the tip end of the protective cover comprises a light-transmissive window part and a wire that is linked to the outer periphery at the tip end of the protective cover.

10 Claims, 8 Drawing Sheets

(56) References Cited

U.S. PATENT DOCUMENTS

| | | | |
|---|---|---|---|
| 2004/0260245 | A1 | 12/2004 | Clem et al. |
| 2005/0251091 | A1 | 11/2005 | Saadat et al. |
| 2006/0149127 | A1 | 7/2006 | Seddiqui et al. |
| 2006/0189844 | A1 | 8/2006 | Tien |
| 2007/0073107 | A1 | 3/2007 | Peartree et al. |
| 2007/0173693 | A1 | 7/2007 | Refael |
| 2007/0173764 | A1 | 7/2007 | Greeson et al. |
| 2007/0185384 | A1 | 8/2007 | Bayer et al. |

FOREIGN PATENT DOCUMENTS

| | | | |
|---|---|---|---|
| JP | 05-057021 | A | 3/1993 |
| JP | 05-253299 | A | 10/1993 |
| JP | 06-315537 | A | 11/1994 |
| JP | 07-080079 | | 3/1995 |
| TW | 589170 | B | 6/2004 |
| WO | 2006111416 | A1 | 10/2006 |
| WO | 2007056452 | A2 | 5/2007 |

OTHER PUBLICATIONS

Office Action issued May 11, 2012 from related Taiwan Patent Application No. 097146526, 3 pgs.

* cited by examiner

ENDOSCOPE SYSTEM FOR GASTROSTOMY CATHETER PLACEMENT

FIELD OF THE INVENTION

The present invention relates to an instrument for confirming the position of an indwelling gastrostomy catheter which is used when a gastrostomy catheter is made indwelling in a patient's body in order to supply fluid such as nutrients and food in fluid form to the patient's stomach, and to a method of confirming the indwelling position.

BACKGROUND OF THE INVENTION

Fluids such as nutrients and food in fluid form are conventionally supplied to people having a reduced capacity for ingesting food orally by themselves due to advanced age or illness (referred to hereinafter as "patients") using a gastrostomy catheter. Such a gastrostomy catheter is provided with a stomach-internal fixed part which is arranged on the inner part of the stomach wall in a hole (gastrostomy hole) for ingestion which is provided in the abdomen of the patient, and a tubular part of which the tip end is linked to the stomach-internal fixed part, and the base end passes through the hole and extends outside the patient's body. When this gastrostomy catheter is attached at the hole which is formed in the patient's body, it is then necessary to confirm whether or not the stomach-internal fixed part of the gastrostomy catheter is indwelling in the correct state inside the stomach.

One method of confirming the indwelling position of the gastrostomy catheter in this case is a method in which an endoscope is inserted into the alimentary canal orally or nasally, and observations are made using the endoscope. There is also another method in which the gastrostomy catheter is made indwelling in the hole in the patient, after which fluid etc. inside the body is sucked out from the gastrostomy catheter by means of a syringe, and the indwelling position of the gastrostomy catheter is confirmed according to the characteristics of the fluid sucked out. With these methods, there are problems with the one in which suction is carried out using a syringe after the gastrostomy catheter has been made indwelling in that it is difficult to judge unless there are marked differences in the characteristics of the fluid etc. sucked out, which leads to poor reliability. Consequently, the method employing an endoscope is preferred in order to more reliably confirm the indwelling position. However, there are problems with the method employing an endoscope such as the high costs of cleaning the endoscope after use and patient discomfort.

In view of these problems, it is possible to significantly reduce the costs of cleaning the endoscope after use by attaching a disposable cover to the endoscope (see, for example, Japanese Unexamined Patent Application Publication H3-292925). This endoscope probe cover (protective cover) is made up of a tube which covers the endoscope probe very closely, and a thread-like body, and it has a structure in which it is possible to split the tube after use by pulling the thread-like body. Consequently, the endoscope probe does not come into direct contact with fluids etc. in various parts of the body and become soiled, which makes sterilizing and cleaning operations largely unnecessary, and therefore the costs entailed by sterilizing and cleaning can be reduced.

However, with the endoscope probe cover described above, there is a risk that soiling adhering to the surface of the tube will then adhere to the endoscope probe when the thread-like body is pulled and the tube is split. In this case also, there are still problems remaining in that if the endoscope probe is inserted into the alimentary canal orally or nasally, this causes discomfort to the patient when the endoscope probe is inserted.

SUMMARY OF THE INVENTION

One embodiment of the present invention is an instrument for confirming the position of an indwelling gastrostomy catheter which comprises a tubular part for running through a hole which is formed between the surface of the skin of a patient and the inner surface of the stomach wall, and extending from outside the patient's body to the inner surface of the stomach wall, and a stomach-internal fixed part capable of linking to the tip end of the tubular part and being arranged at the inner surface of the stomach wall, the fixed part having a through-hole adapted to receive the tubular part therethrough said instrument comprising a fiberscope, with which it is possible to observe the inner surface of the stomach wall, adapted to run through the inside of the tubular part so that the tip end thereof projects from the through-hole of the stomach-internal fixed part, and a protective cover adapted to pass through the gastrostomy catheter together with the fibrescope, in a state in which the fibrescope is covered, the cover including a light-transmissive window part at a tip end thereof which allows observation of the inner surface of the stomach wall by means of the fiberscope.

Another aspect of this invention is an inventive method of confirming the position of an indwelling gastrostomy catheter which comprises a tubular part for running through a hole which is formed between the surface of the skin of the patient and the inner surface of the stomach wall, and extending from outside the patient's body to the inner surface of the stomach wall, and a stomach-internal fixed part capable of linking to the tip end of the tubular part and being arranged at the inner surface of the stomach wall, the fixed part having a through-hole adapted to receive the tubular part therethrough said method comprising: making the gastrostomy catheter indwelling, in which the gastrostomy catheter is made indwelling in the hole; covering the fibrescope, in which the fibrescope is covered by a protective cover; inserting the fiberscope covered by the protective cover inside the tubular part, with the tip end portion thereof projecting from the through-hole of the stomach-internal fixed part; confirming the indwelling position, in which the inner surface of the stomach wall observed by means of the fibrescope is checked; withdrawing the fibrescope, in which the fibrescope which has been covered by the protective cover is withdrawn from the gastrostomy catheter; and removing the protective cover, in which the fibrescope is withdrawn from the protective cover.

DESCRIPTION OF FIGURE NOTATIONS

Figure 1:
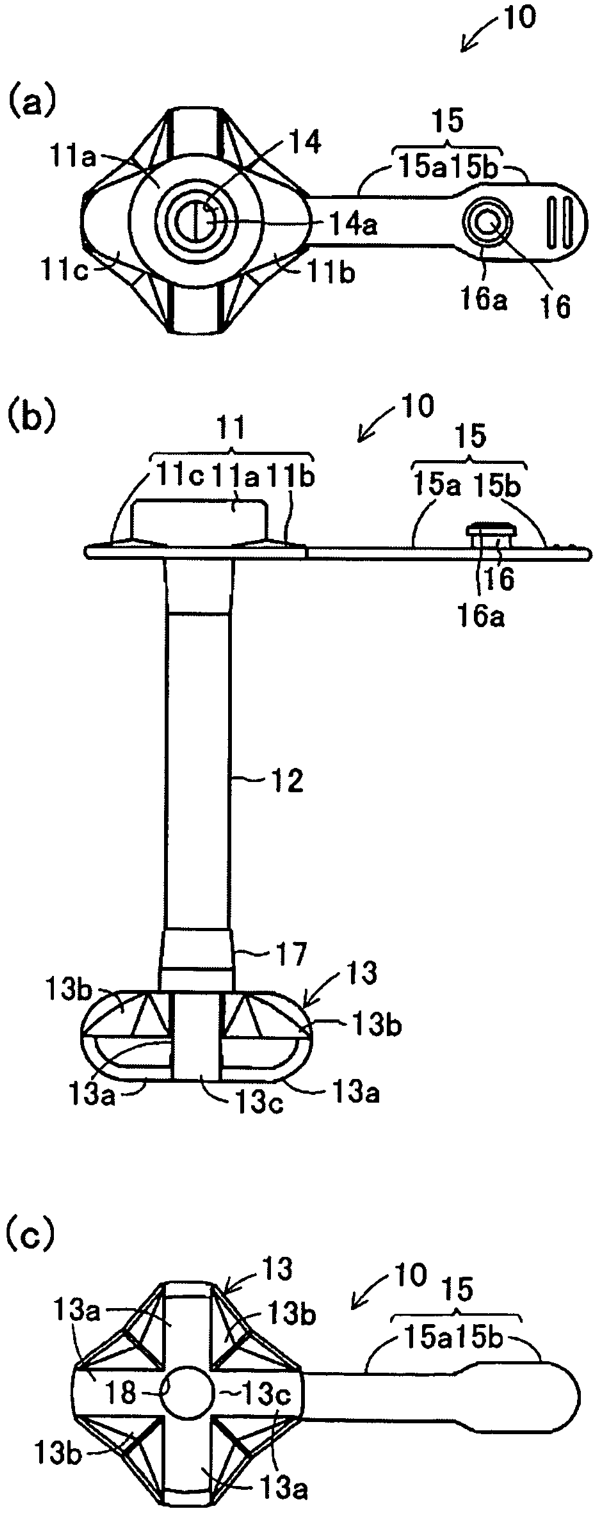
FIG. 1 shows a gastrostomy catheter, where (a) is a plan view, (b) is a front view, and (c) is a bottom view.

10: Gastrostomy catheter
12: Tubular part
13: Stomach-internal fixed part
18: Through-hole
20: Instrument for confirming the indwelling position
23: Fiberscope
24: Protective cover
24*a*: Window part
24*c*: Wire
AW: Abdominal wall
SW: Stomach wall

DETAILED DESCRIPTION OF THE INVENTION

Figure 2:
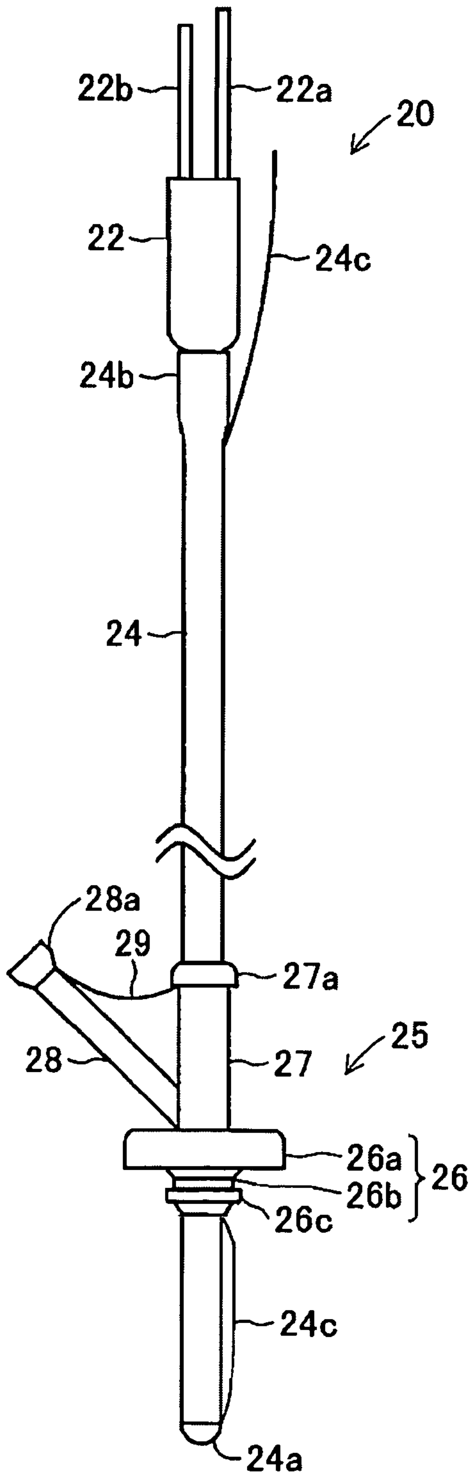
FIG. 2 is a front view showing the inventive instrument for confirming the indwelling position according to one embodiment.

One embodiment of the present invention will be described below with reference to the figures. FIG. 1 shows a gastrostomy catheter 10 pertaining to this mode of embodiment, and FIG. 2 shows an instrument 20 for confirming the indwelling position in order to confirm the indwelling position of the gastrostomy catheter 10. The gastrostomy catheter 10 comprises an external fixed part 11, a tubular part 12 which is linked to the centre of the lower end surface of the external fixed part 11, and a stomach-internal fixed part 13 which is attached to the lower end of the tubular part 12, all these components being made of a soft plastic material such as polyurethane or silicone. In the description that follows, the external fixed part 11 will be taken as the upper side, and the stomach-internal fixed part 13 will be taken as the lower side.

The external fixed part 11 comprises an insertion opening 11*a* which is annular and fairly thick, and projecting pieces 11*b*, 11*c* of which the outline is elliptical and includes the insertion opening 11*a*, these pieces projecting at both sides from the lower end of both side parts of the insertion opening 11*a*, when seen as a plane. The function of these projecting pieces 11*b*, 11*c* is to prevent the gastrostomy catheter 10 from being pulled into the stomach S (see FIGS. 6 to 8). A valve body 14*a* which is formed with a central slit is then provided on the inner peripheral surface of an insertion hole 14 which is formed in the centre of the insertion opening 11*a*, passing through vertically. Furthermore, an engagement groove is formed along the circumference at the upper side of the valve body 14*a* on the inner peripheral surface of the insertion hole 14, although this is not depicted. A cover part 15 for closing off the insertion hole 14 of the insertion opening 11*a* is then joined to the tip end side of the projecting piece 11*b*.

The cover part 15 comprises an elongate strip-shaped linking part 15*a* which is linked to the end part of the projecting piece 11*b*, and a broad part 15*b* which is shorter and wider than the strip-shaped linking part 15*a*, and is formed at the tip end of the strip-shaped linking part 15*a*. A stopper part 16 shaped like a column which is short in the axial direction is then provided on the broad part 15*b*. The strip-shaped linking part 15*a* is flexible, and it can flex so as to vertically rotate, or bend at a sharp angle, with the linking part to the projecting piece 11*b* at the centre. The stopper part 16 is provided on the strip-shaped linking part 15*a* side portion of the broad part 15*b*, so as to face the insertion hole 14 when the strip-shaped linking part 15*a* is bent to position the broad part 15*b* above the insertion opening 11*a*.

The stopper part 16 is formed with a columnar shape which can fit into the insertion hole 14, and it is provided on its outer peripheral surface with an annular projection 16*a* running along its periphery, this projection being able to detachably engage with the engagement groove formed on the inner peripheral surface of the insertion hole 14. Accordingly, it is possible to engage the engagement groove with the annular projection 16*a* by bending the strip-shaped linking part 15*a* so that it is upwardly inverted, and pushing the stopper part 16 into the insertion hole 14, and this makes it possible to close off the insertion hole 14 of the insertion opening 11*a* in an airtight manner. It is also possible to open the insertion hole 14 of the insertion opening 11*a* by pulling the broad part 15*b* to release the fitting between the stopper part 16 and the insertion hole 14.

The tubular part 12 is formed as a cylindrical shape, and a supply channel (not depicted) for allowing the passage of fluids such as nutrients and food in fluid form is formed inside it; the upper end of the supply channel links in communication with the insertion hole 14 of the external fixed part 11. The stomach-internal fixed part 13 is connected to the tubular part 12 via a connection part 17 which is fixed to the lower end of the tubular part 12. Said connection part 17 is formed as a cylinder for covering the outer peripheral surface of the tubular part 12 and is integrally formed with the stomach-internal fixed part 13. Said connection part 17 is then attached to the lower end of the tubular part 12, in a state in which it cannot be removed from the tubular part 12.

The stomach-internal fixed part 13 comprises four strip-shaped linking parts 13*a* which are linked to the edge of a lower end opening of the connection part 17 and extend in four directions, four linking film parts 13*b* which are provided between the upper parts of each of the linking parts 13*a* and form a roughly dome-shaped stomach wall contact part with the four linking parts 13*a*, and a converging part 13*c* where the tip ends of all of the linking parts 13*a* converge. The four linking parts 13*a* comprise strip-shaped members which are bent into substantially semi-circular shapes which split into four directions from the lower end of the connection part 17, respectively extending downwards from the horizontal, after which they converge below the central axis of the tubular part 12, linking to form the converging part 13*c*. That is to say, the converging part 13*c* allows each of the linking parts 13*a* to link by joining the lower ends of all of the linking parts 13*a*, and it is also positioned by all of the linking parts 13*a* below the central axis of the tubular part 12.

Moreover, the stomach-internal fixed part 13 which comprises the linking parts 13*a*, linking film parts 13*b* and the converging part 13*c* is integrally formed together with the connection part 17. Furthermore, all of the linking parts 13*a* and linking film parts 13*b* are made of a soft, flexible, elastic material, and the overall roughly spherical shape is normally maintained by means of this elasticity, as shown in FIG. 1, but the shape can be extended to make it straight and elongate by pulling the converging part 13*c* downwards. Furthermore, spaces formed between the lower parts of each of the linking parts 13*a* form channels for the passage of fluids such as nutrients and food in fluid form sent out from the supply channel of the tubular part 12 into the stomach S. A through-hole 18 is additionally formed in the centre of the converging part 13*c*. The stomach-internal fixed part 13 configured in this manner is positioned on the inner surface of the patient's stomach wall SW (see FIGS. 6 to 8) and its function is to prevent the gastrostomy catheter 10 from being removed from the patient's body.

Figure 3:
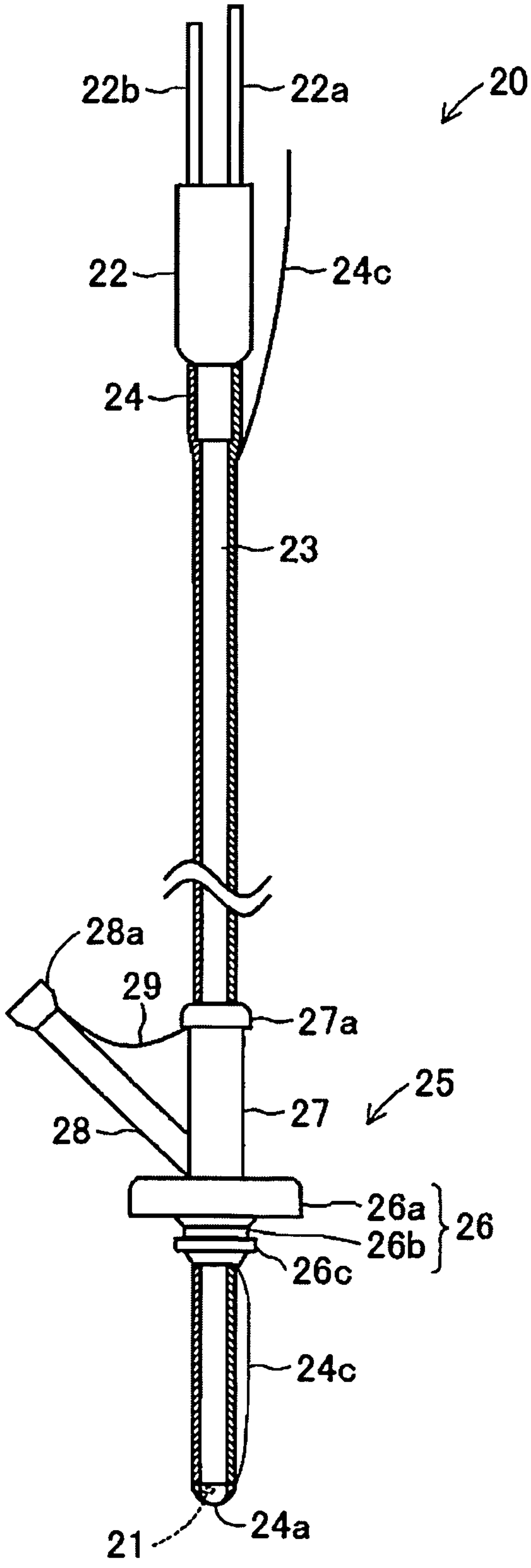
FIG. 3 is a partial cutaway view in section, in which part of the instrument for confirming the indwelling position shown in FIG. 2 has been cut away.
Figure 4:
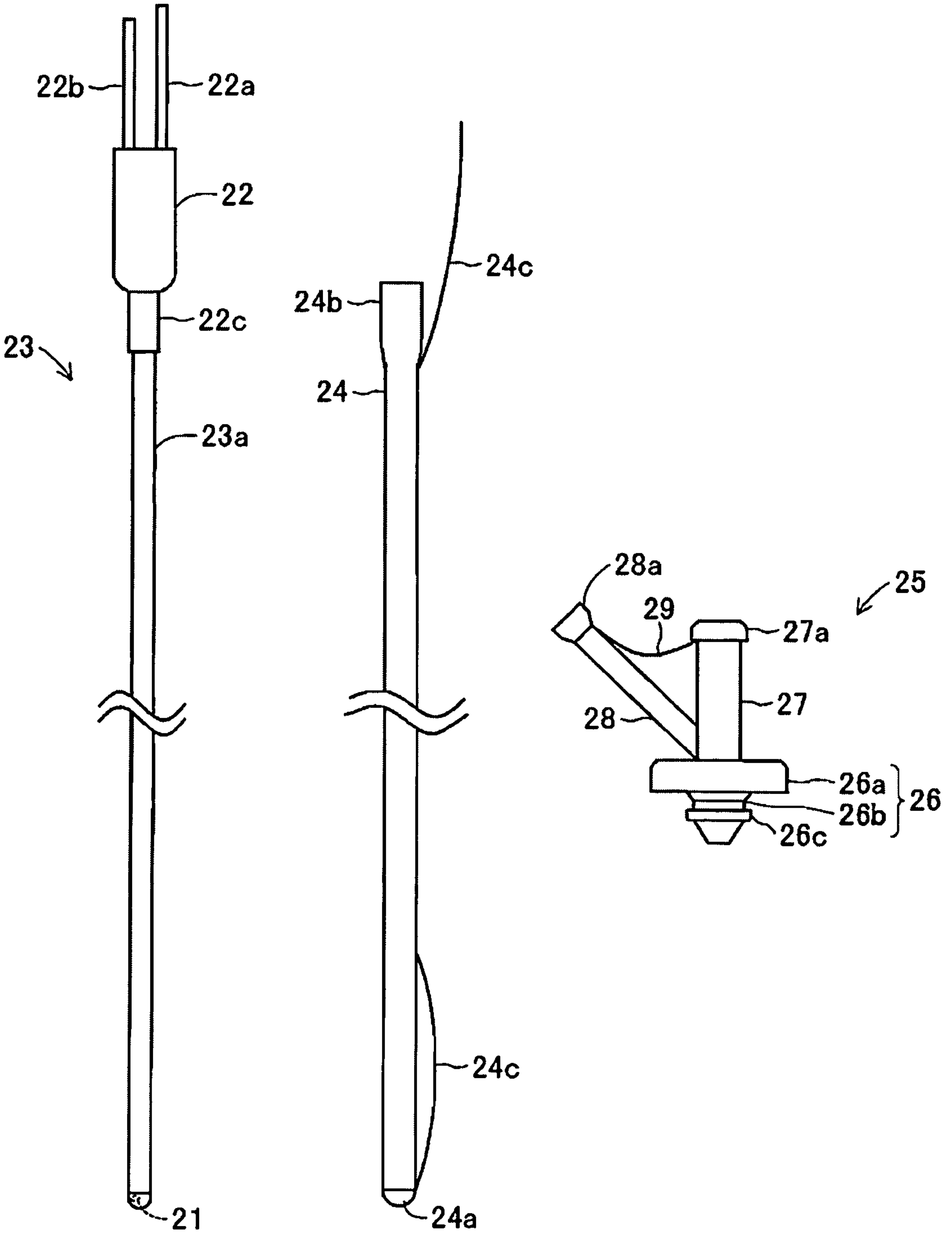
FIG. 4 is an oblique disassembled view showing each of the members which make up the instrument for confirming the indwelling position.
Figure 5:
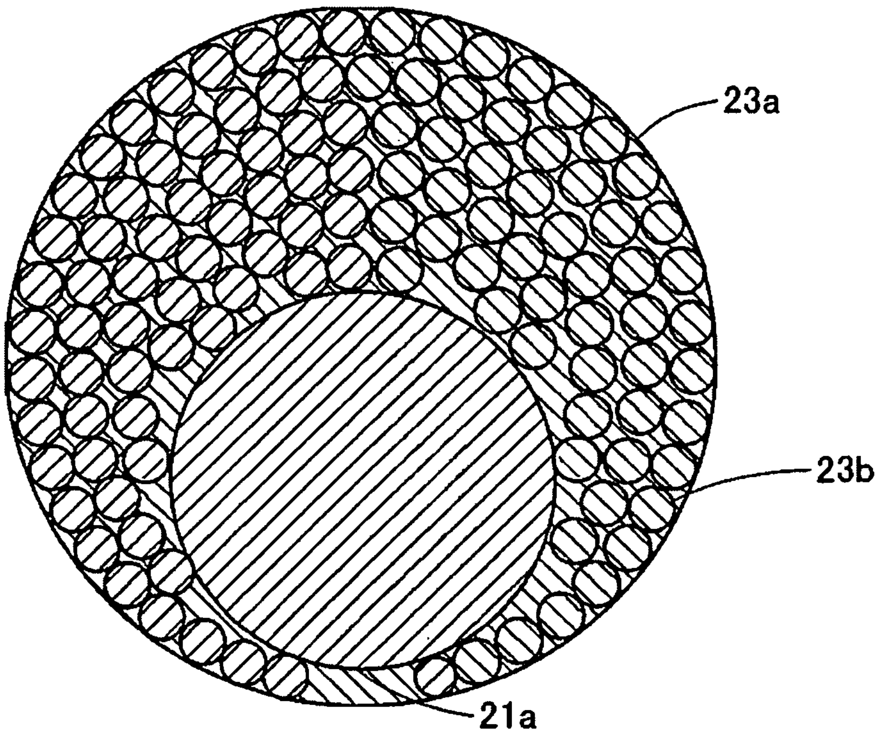
FIG. 5 is a view in cross section of a fiberscope shaft.

As shown in FIGS. 2 to 4, the instrument 20 for confirming the indwelling position comprises a fibrescope 23 which has a configuration in which a lens 21 is attached to the tip end of a fibrescope shaft 23*a* and a connecting part 22 is attached to the rear end thereof, a protective cover 24, and a connection fitting 25. As shown in FIG. 5, the fibrescope shaft 23*a* is flexible and it is configured by a bundle of fibres comprising a plurality of light guides 23*b* for irradiating light onto the stomach wall SW, and an image guide 21*a* for sending images via the lens 21. The connection part 22 is connected to wiring 22*a* for connecting the image guide 21*a* to an image display device (not depicted), and wiring 22*b* for connecting the light guides 23*b* to a light source device (not depicted).

The lens 21 sends images obtained by the irradiation of the light guides 23*b* to the image display device, via the image guide 21*a* and the wiring 22*a*. In other words, the light guides 23*b* irradiate the inner surface of the stomach wall SW with light sent from the light source device to make observation possible, and the image guide 21*a* sends the light which is reflected from the inner surface of the stomach wall SW and focused by means of the lens 21 to the image display device. The image display device then enlarges the images sent and displays them on an image display part provided in the image display device.

Furthermore, the protective cover 24 is flexible and is such that its tip end is closed off by a light-transmissive window part 24*a*, and its base end 24*b* on the opening side is configured by a tube of somewhat larger diameter than the other portions. Said protective cover 24 is formed to be of a thickness which can cover and fix the fibrescope shaft 23*a*, and it is prevented from being removed from the fibrescope shaft 23*a* by inserting a tip-end narrow-diameter part 22*c* of the connection part 22 into the base end 24*b*. In this state, the instrument is configured so that the lens 21 is in contact with the inner surface of the window part 24*a*.

Furthermore, the tip end of a wire 24*c* which acts as the linear member pertaining to the present invention is fixed to the edge of the window part 24*a* on the outer peripheral surface of the protective cover 24. A wire lumen (not depicted) for the passage of the wire 24*c* through the lower end region of the base end 24*b* is formed from a portion of specified length (the length required to bend the protective cover 24) above the tip end on the peripheral surface of the protective cover 24. The wire 24*c* extends upwards and outside of the tip end of the protective cover 24, after which it passes through inside the wire lumen and extends outside.

The connection fitting 25 is attached to the gastrostomy catheter 10 to provide smoother insertion of the protective cover 24 etc. into the gastrostomy catheter 10, and it is configured by a connection part 26, insertion opening 27 and an air supply opening 28. The connection part 26 is configured by a substantially cylindrical engagement part 26*b* which is formed in the centre of the lower surface of an annular connection part main body 26*a*, and an insertion hole for allowing the insertion of the protective cover 24 is formed therein. Furthermore, the connection part main body 26*a* is formed with an annular shape which is substantially the same size as the insertion opening 11*a* of the gastrostomy catheter 10, and the engagement part 26*b* is formed with a cylindrical shape having four different levels.

The engagement part 26*b* is made up of an uppermost level in which the outer peripheral surface which has a larger diameter at its upper part than its lower part has an oblique surface, a second level which has the same diameter as the lower part of the uppermost level, a third level which has substantially the same diameter as the upper part of the uppermost level, and a lowermost level in which the outer peripheral surface which has substantially the same diameter as the second level at its upper part, and a smaller diameter at its lower part than its upper part has an oblique surface. The third level of the engagement part 26*b* configures an annular projection 26*c* which is able to detachably engage with the engagement groove formed in the insertion hole 14 of the gastrostomy catheter 10, and when the annular projection 26*c* engages with the engagement groove, a state of air-tightness is achieved between the engagement part 26*b* and the peripheral surface of the insertion hole 14.

The insertion opening 27 is formed with a cylindrical shape and an insertion hole enabling the insertion of the protective cover 24 is formed therein, an annular reinforcing rib 27*a* being formed on the edge of the opening at the upper end. Furthermore, the insertion hole formed inside the insertion opening 27 and the insertion hole formed inside the connection part 26 have the same diameter and are also coaxially linked in communication. The air supply opening 28 is formed as a cylindrical shape extending obliquely upwards from the lower end of the insertion opening 27 in a state in which it is inclined at approximately 45° to the insertion opening 27, and it is narrower in diameter than the insertion opening 27. An annular reinforcing rib 28*a* is furthermore formed on the edge of the opening at the upper end of the air supply opening 28.

An air supply device (not depicted) is connected to the reinforcing rib 28*a* of said air supply opening 28, and air which is supplied from the air supply device passes through inside the air supply opening 28 and is sent to the lower end inside the insertion opening 27. Furthermore, an airflow channel (not depicted) for allowing the passage of air is formed between the lower end inside the insertion opening 27 and the lower end inside the connection part 26; air sent to the lower end inside the insertion opening 27 is released to the outside from the lower end of the connection part 26.

A substantially triangular sheet-like reinforcing grip part 29 for strengthening the area between the insertion opening 27 and the air supply opening 28 and also for facilitating holding of the connection fitting 25 with the hand is formed between the insertion opening 27 and the air supply opening 28. The instrument 20 for confirming the indwelling position shown in FIG. 2 is assembled by covering the fibrescope shaft 23*a* with the protective cover 24, and by passing the protective cover 24 etc. in this state together with the wire 24*c* through the insertion hole formed inside the insertion opening 27 and the connection part 26 of the connection fitting 25.

Figure 6:
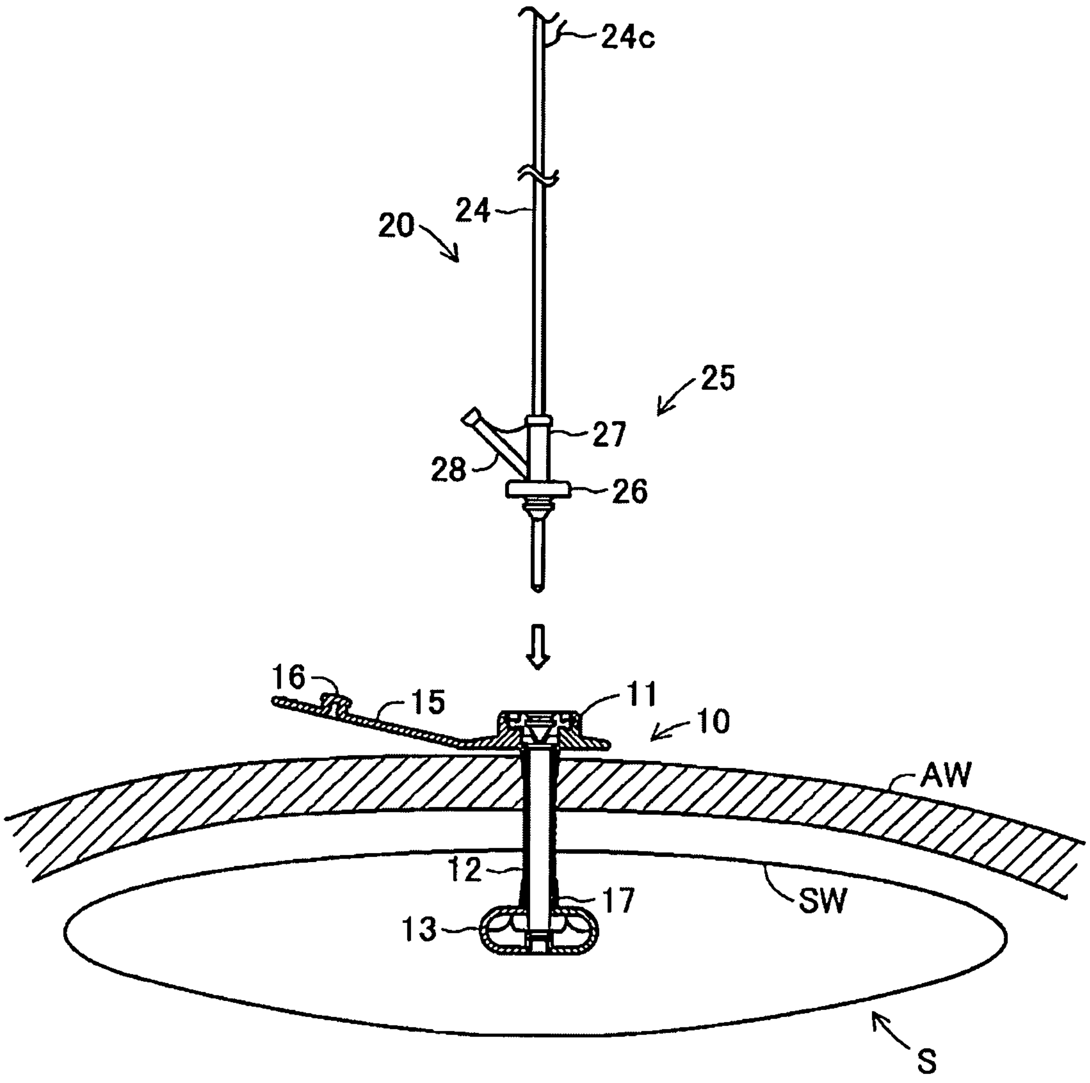
FIG. 6 is a partial cutaway view showing a state in which the instrument for confirming the indwelling position is positioned above the gastrostomy catheter which is indwelling in the patient's body.

A description of the method of confirming the indwelling position of the gastrostomy catheter 10 using the instrument 20 for confirming the indwelling position configured in the manner described above will be given next, with reference to FIGS. 6 to 8. FIG. 6 shows a state in which the gastrostomy catheter 10 is indwelling in a hole provided in the abdominal wall AW and the stomach wall SW of a patient, where said gastrostomy catheter 10 is made indwelling in the hole using a specific instrument for fitting it. A description of the structure and the method of making this fitting instrument indwelling will be omitted here. In the state shown in FIG. 6, the stopper part 16 of the gastrostomy catheter 10 is removed from the insertion hole 14 to open the upper end of the insertion hole 14. Furthermore, the instrument 20 for confirming the indwelling position is positioned above the gastrostomy catheter 10, and the instrument 20 for confirming the indwelling position which is in this state is moved down in the direction of the arrow in the figures so that the protective cover 24 projecting from the lower end of the connection fitting 25 is inserted into the insertion hole 14 of the gastrostomy catheter 10 together with the fibrescope 23.

Figure 7:
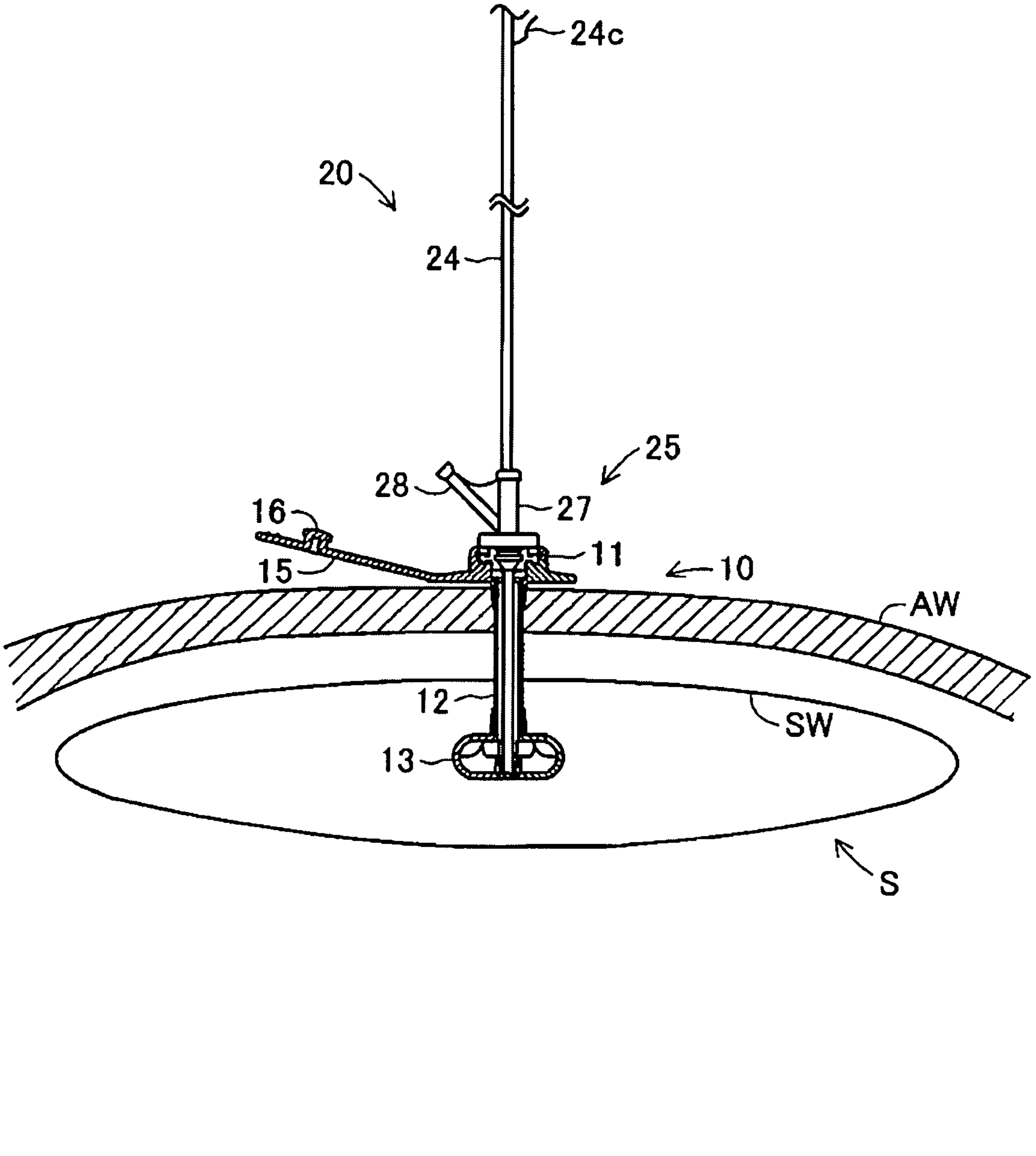
FIG. 7 is a partial cutaway view showing a state in which the instrument for confirming the indwelling position is inserted into the gastrostomy catheter which is indwelling in the patient's body.

At this time, an operator holds both sides of the insertion opening 11*a* on the gastrostomy catheter 10 with one hand, and holds the reinforcing grip part 29 of the connection fitting 25 with the other hand, and pushes the connection fitting 25 into the gastrostomy catheter 10. As shown in FIG. 7, this makes it possible to engage the connection fitting 25 with the gastrostomy catheter 10. The engagement in this case is brought about by the engagement of the annular projection 26*c* of the connection fitting 25 with the engagement groove of the gastrostomy catheter 10, and a state of air-tightness is achieved between the connection fitting 25 and the gastrostomy catheter 10. The protective cover 24 is then further inserted towards the lower side of the gastrostomy catheter 10 together with the fibrescope 23, and the lower portion of the protective cover 24 projects downwards from the through-hole 18 formed at the lower end of the gastrostomy catheter 10. It should be noted that the protective cover 24 and the fibrescope 23 may pass inside the connection fitting 25 after the connection fitting 25 has been connected to the gastrostomy catheter 10.

Figure 8:
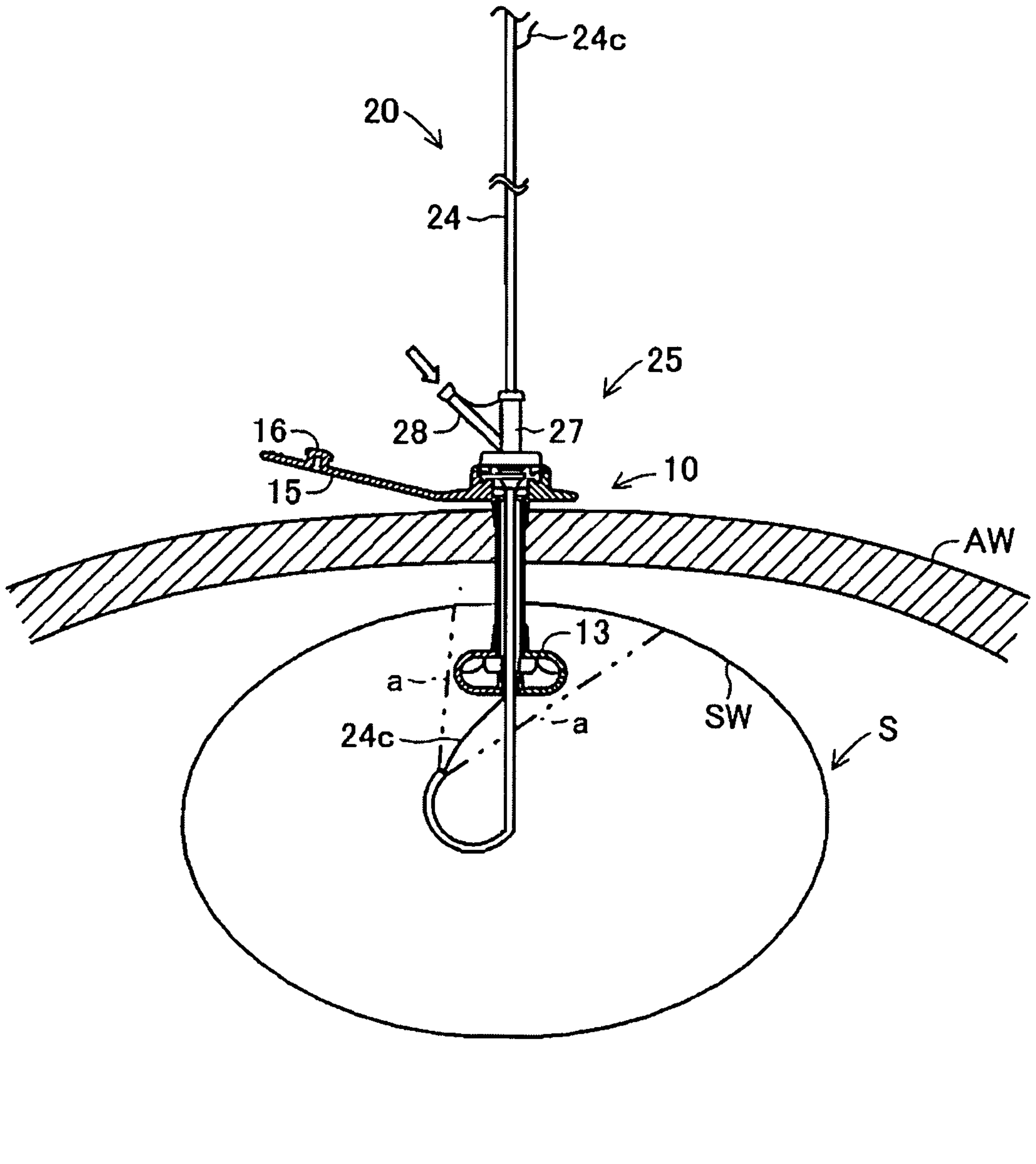
FIG. 8 is a partial cutaway view showing a state in which the indwelling position of the gastrostomy catheter is confirmed using the instrument for confirming the indwelling position.

Next, air is supplied from the air supply device to inside the air supply opening 28, and this air is sent into the stomach S from the connection part 26 via the tubular part 12 of the gastrostomy catheter 10. This allows the stomach S to expand, as shown in FIG. 8. In this state, light is generated by means of the light source device, whereby light passes through the wiring 22*b* and the light guides 23*b* of the fibrescope shaft 23*a*, and is irradiated towards the stomach wall SW, as shown in FIG. 8. Furthermore, in this case, the tip end portion of the protective cover 24 can be made to flex together with the fibrescope shaft 23*a* so that it is possible to change the position of irradiation of the stomach wall SW by the light guides 23*b*, and this is achieved by pulling the wire 24*c*, as required.

The range shown by the two-dot chain line in FIG. 8 shows the range of light irradiation by the light guides 23*b*. Light which is irradiated by means of the light guides 23*b* and reflected off the stomach wall SW is focused by the lens 21, after which it is sent to the image display device by way of the image guide 21*a* and the wiring 22*a* of the fibrescope shaft 23*a*. Images which are sent to the image display device are enlarged in the image display part of the image display device, and therefore it is possible to confirm whether or not the stomach-internal fixed part 13 of the gastrostomy catheter 10 is positioned in the correct state inside the stomach S, from the images displayed in said image display part. If it is possible to confirm that the gastrostomy catheter 10 is indwelling in the correct state, an operation is carried out in which the instrument 20 for confirming the indwelling position is removed from the gastrostomy catheter 10, and also the protective cover 24 is removed from the fibrescope shaft 23*a*.

In this operation, the protective cover 24 is first of all pulled upwards together with the fibrescope 23 in a state in which the force pulling on the wire 24*c* has been released, and then in the state shown in FIG. 7, the engagement between the annular projection 26*c* of the connection fitting 25 and the engagement groove of the gastrostomy catheter 10 is released. The protective cover 24 and the fibrescope 23 are then removed from the gastrostomy catheter 10 by pulling them upwards together with the connection fitting 25. In addition, the connection fitting 25 is removed from the protective cover 24 etc., after which the fibrescope shaft 23*a* etc. is pulled out of the protective cover 24. The protective cover 24 is then disposed of, and the fibrescope 23 can be reused next time.

At this time, the lens 21 and the fibrescope shaft 23*a* do not come into contact with the liquids and residues inside the patient's body and stomach S, so they are not soiled and there is no need for the most part to clean or sterilize them. Furthermore, when the fibrescope 23 is reused, the fibrescope shaft 23*a* is covered with a new protective cover 24. Moreover, in the operation described above, the engagement between the annular projection 26*c* of the connection fitting 25 and the engagement groove of the gastrostomy catheter 10 is released, and the protective cover 24 and the fibrescope 23 are removed from the gastrostomy catheter 10 together with the connection fitting 25, but it is also possible to remove the protective cover 24 etc. from the connection fitting 25, and then to release the engagement between the annular projection 26*c* of the connection fitting 25 and the engagement groove of the gastrostomy catheter 10.

Furthermore, when nutrient fluid is supplied to the patient's stomach S, for example, by way of the gastrostomy catheter 10 which is indwelling in the patient's body, a connector for a tube extending from a container housing the nutrients is connected to the insertion hole 14 of the gastrostomy catheter. In this state, nutrients are supplied to the patient by way of the tube and the gastrostomy catheter 10. At this time, nutrients coming out of the tubular part 12 pass from the stomach-internal fixed part 13 through each of the linking parts 13*a*, and enter the stomach S. Furthermore, after use, the tube from the container of nutrients is removed from the insertion hole 14 of the gastrostomy catheter 10, and the insertion hole 14 is closed using the stopper part 16. Then, when it becomes necessary to replace the gastrostomy catheter 10 after regular periods of use, it can be replaced with a new gastrostomy catheter 10. In this case also, the indwelling position of the gastrostomy catheter 10 can be confirmed using the instrument 20 for confirming the indwelling position which has been described above.

In this way, the inventive instrument 20 for confirming the indwelling position of a gastrostomy catheter is provided with a protective cover 24, and the fibrescope shaft 23*a* is covered by this protective cover 24, and they pass through the gastrostomy catheter 10. Consequently, there is no discomfort for the patient caused by the fitting of the fibrescope 23 and the protective cover 24 to the patient's body. Furthermore, after the indwelling position of the gastrostomy catheter 10 has been confirmed, the fibrescope 23 etc. are pulled out from the gastrostomy catheter 10, and then the fibrescope 23 is pulled out from the protective cover 24, whereby the fibrescope shaft 23*a* does not become soiled with gastric juices etc.

As a result, there is virtually no need to clean or sterilize the fibrescope 23, making expenses for sterilization and cleaning largely unnecessary, and also making it possible to extend the lifespan of the fibrescope 23. Furthermore, the wire 24*c* is linked to the tip end of the protective cover 24, and the tip end of the protective cover 24 projects from the through-hole 18 of the stomach-internal fixed part 13, and in this state the tip end portion of the protective cover 24 can be made to flex together with the fibrescope shaft 23*a* by pulling the wire 24*c* so that it is possible to change the direction of irradiation by the light guides 23*b* and the direction of focus of the lens 21. This means that it is possible to change the direction of irradiation and the direction of focus with a simple operation, and it is possible to more reliably confirm the indwelling position.

Furthermore, the inventive instrument for confirming the indwelling position of a gastrostomy catheter is not limited to the embodiment described above, and appropriate modifications may be implemented within the technical scope of the present invention. For example, in the embodiment described above, an external fixed part 11 is provided on the gastrostomy catheter 10, but a gastrostomy catheter which is not provided with an external fixed part 11 may also be used. In this case the connection fitting 25 may also be dispensed with. It is also possible to use other devices having similar functions instead of the image display device and light source device, etc. In addition, in the embodiment described above, the tip end portion of the protective cover 24 is made to flex together with the fibrescope shaft 23*a* by pulling the wire 24*c*, but the wire 24*c* may be configured by a rigid material, and the tip end portion of the protective cover 24 may be made to flex together with the fibrescope shaft 23*a* by pushing the wire 24*c*.

With the present invention configured in the manner described above, the fiberscope which is used as an endoscope may be covered by a protective cover and passed through inside the gastrostomy catheter. In this way, the fiberscope is inserted together with the protective cover from the gastrostomy catheter which is already indwelling in the patient's body, reaching the inner surface of the stomach wall, and therefore there is no discomfort for the patient caused by the insertion of the fiberscope and the protective cover. Furthermore, it is possible to reduce the diameter of the endoscope by using a fiberscope as the endoscope, as a result of which the endoscope passes through the gastrostomy catheter more easily.

Furthermore, when the indwelling position of the gastrostomy catheter is confirmed, the protective cover and the fiberscope can then be pulled out of the gastrostomy catheter together, after which the fiberscope is pulled out of the protective cover, whereby the fiberscope can be removed from the patient's body without any soiling of the fiberscope with gastric juices etc. As a result, there is virtually no need to clean or sterilize the fiberscope, making expenses for sterilization and cleaning largely unnecessary, and also making it possible to extend the lifespan of the fiberscope. In addition, the tip end of the protective cover facing the tip end of the fiberscope consists of a window part which allows light transmission, and therefore there is no reduction in the observational accuracy of the stomach wall by the fiberscope due to the protective cover.

Another aspect of one embodiment of the present invention is that when a linear member is linked to the outer periphery at the tip end of the protective cover, and the tip end of the protective cover is projecting from the through-hole of the stomach-internal fixed part, the tip end portion of the protective cover can be made to flex together with the fiberscope so that it is possible to change the observation direction of the fiberscope, by operation of the rear end portion of the linear member. By virtue of this, it is possible to change the direction of observation of the lens using a simple operation, and this makes it possible to confirm the indwelling position more reliably. In this case, it is possible to confirm the direction of the through-hole of the stomach-internal fixed part using the fiberscope. Furthermore, the fiberscope is such that it flexes under the action of the protective cover, and therefore the fiberscope itself can be made with a simple structure. Because of this, it is possible to reduce the number of components of the fiberscope itself which might break down. The operations of the rear end portion of the linear member in this case include pushing and pulling operations of the linear member.

What is claimed is:

1. An instrument for confirming a position of an indwelling gastrostomy catheter which comprises a tubular part for extending through a hole formed between a surface of skin of a patient's body and an inner surface of a stomach wall of the patient's body, and extending from outside the patient's body to the inner surface of said stomach wall, and a stomach-internal fixed part capable of linking to a tip end of said tubular part and arranged at the inner surface of said stomach wall, the fixed part having a through-hole adapted to receive the tubular part therethrough, said instrument for confirming the position of an indwelling gastrostomy catheter comprising:

a fiberscope for observing the inner surface of the stomach wall adapted to extend through the through-hole of said tubular part so that a tip end of the fiberscope projects from the through-hole of said stomach-internal fixed part;

a protective cover having a closed distal end and adapted to pass through said gastrostomy catheter while covering said fiberscope, the fiberscope being removably received in the protective cover;

a linear member connectable to an outer periphery surface of the protective cover at a closed distal end of said protective cover so that when the distal end of said protective cover projects from the through-hole of said stomach-internal fixed part, the distal end of said protective cover flexes with said fiberscope to change an observation direction of the fiberscope by direct manual manipulation of a proximal free end of said linear member; and a lumen for passage of the linear member within the protective cover, wherein the protective cover includes a lower end region having a length defined as a distance between the closed end and an entrance to the lumen, the length selected to allow the instrument to flex the protective cover with the fiberscope located within the protective cover such that the closed distal end can be oriented to face a location of the hole in the inner surface of the stomach wall through which the tubular part of the gastrostomy catheter extends.

2. An instrument for confirming the position of an indwelling gastrostomy catheter according to claim 1, wherein the proximal free end of said linear member is configured to be grasped by a user and pulled to change the observation direction of the fiberscope.

3. An instrument for confirming the position of an indwelling gastrostomy catheter according to claim 1, wherein said linear member is rigid so that the proximal free end can be grasped by a user and pushed to change the observation direction of the fiberscope.

4. An instrument for confirming the position of an indwelling gastrostomy catheter according to claim 1, further comprising a light transmissive window located at the closed distal end of the protective cover.

5. An instrument for confirming the position of an indwelling gastrostomy catheter according to claim 4, wherein the fiberscope includes a distal end and a lens located at the distal end of the fiberscope, and wherein a direction of focus of the lens is in a direction of the location of the hole when the linear member is employed to orient the closed distal end to face the location of the hole.

6. An instrument for confirming the position of an indwelling gastrostomy catheter according to claim 5, wherein an accuracy of observation of the stomach wall by the fiberscope is maintained through a range of motion of the closed distal end including an orientation in which the closed distal end faces the location of the hole.

7. An instrument for confirming the position of an indwelling gastrostomy catheter according to claim 5, wherein the linear member is attached to an edge of the light transmissive window.

8. An instrument for confirming a position of an indwelling gastrostomy catheter which comprises a tubular part for extending through a hole formed between a surface of skin of a patient's body and an inner surface of a stomach wall of the patient's body, and extending from outside the patient's body to the inner surface of said stomach wall, and a stomach-internal fixed part capable of linking to a tip end of said tubular part and arranged at the inner surface of said stomach wall, the fixed part having a through-hole adapted to receive the tubular part therethrough, said instrument for confirming the position of an indwelling gastrostomy catheter comprising:

a fiberscope for observing the inner surface of the stomach wall adapted to extend through the through-hole of said tubular part so that a tip end of the fiberscope projects from the through-hole of said stomach-internal fixed part;

a protective cover having a closed distal end and adapted to pass through said gastrostomy catheter while covering said fiberscope, the fiberscope being removably received in the protective cover;

a linear member connectable to an outer periphery surface of the protective cover at a closed distal end of said protective cover so that when the distal end of said protective cover projects from the through-hole of said stomach-internal fixed part, the distal end of said protective cover flexes with said fiberscope to change an observation direction of the fiberscope by direct manual manipulation of a proximal free end of said linear member; and a light transmissive window located at the closed distal end of the protective cover, wherein the linear member is attached to an edge of the light transmissive window.

9. The instrument for confirming the position of an indwelling gastrostomy catheter according to claim 8, wherein the protective cover includes a lower end region having a length selected to allow the instrument to flex the protective cover with the fiberscope located within the protective cover such that the closed distal end can be oriented to face a location of the hole in the inner surface of the stomach wall through which the tubular part of the gastrostomy catheter extends, wherein the linear member is external to the protective cover along the length of the lower end region.

10. The instrument for confirming the position of an indwelling gastrostomy catheter according to claim 9, further comprising a lumen for passage of the linear member within the protective cover above the lower end region, and an entrance to the lumen located in the protective cover.

* * * * *